United States Patent [19]

Meyer

[11] 4,177,347

[45] Dec. 4, 1979

[54] DISTILBENYL-OXDIAZOLES

[75] Inventor: Hans R. Meyer, Binningen, Switzerland

[73] Assignee: Ciba-Geigy Corporation, Ardsley, N.Y.

[21] Appl. No.: 908,600

[22] Filed: May 23, 1978

Related U.S. Application Data

[63] Continuation of Ser. No. 749,643, Dec. 10, 1976, abandoned, which is a continuation of Ser. No. 585,540, Jun. 10, 1975, abandoned.

[30] Foreign Application Priority Data

Jun. 12, 1974 [CH] Switzerland ........................ 8031/74
Jun. 12, 1974 [CH] Switzerland ........................ 8038/74

[51] Int. Cl.$^2$ .......................................... C07D 271/06
[52] U.S. Cl. .................................. 542/459; 542/460; 542/462; 252/301.24
[58] Field of Search ....................... 542/459, 460, 462

[56] References Cited

U.S. PATENT DOCUMENTS

| | | | |
|---|---|---|---|
| 3,779,931 | 12/1973 | Fries et al. | 252/99 |
| 3,825,534 | 7/1974 | Weber et al. | 542/464 |
| 3,843,633 | 10/1974 | Weber et al. | 542/458 |

FOREIGN PATENT DOCUMENTS 811155  4/1969  Canada .

Primary Examiner—Arthur F. Demers
Attorney, Agent, or Firm—Prabodh I. Almaula

[57] ABSTRACT

Distilbenyl-oxadizoles, a process for their preparation, their use for optically brightening organic materials as well as detergents containing them are disclosed.

11 Claims, No Drawings

DISTILBENYL-OXDIAZOLES

This is a continuation of application Ser. No. 749,643 filed on Dec. 10, 1976 now abandoned, which is a continuation of application Ser. No. 585,540, filed on June 10, 1975, now abandoned.

The present invention relates to distilbenzyl-oxdiazoles, a process for their manufacture and their use as optical brighteners for high-molecular organic materials.

The distilbenzyl-oxdiazoles according to the invention correspond to the formula

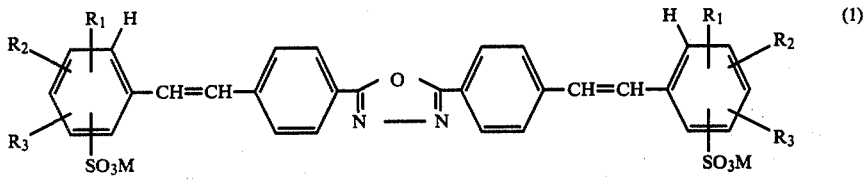

wherein $R_1$ denotes hydrogen, alkyl having 1 to 4 carbon atoms, alkoxy having 1 to 4 carbon atoms, chlorine, sulpho, sulphophenyl, cyano, carboxyl or carbalkoxy having 2 to 6 carbon atoms, $R_2$ denotes hydrogen, alkyl having 1 to 4 carbon atoms, alkoxy having 1 to 4 carbon atoms, or chlorine, $R_3$ denotes hydrogen or alkyl having 1 to 4 carbon atoms and M denotes a hydrogen ion, alkali metal ion, alkaline earth metal ion, ammonium ion or amine salt ion.

"Carboxyl" and "sulpho" are to be understood in each case as the radicals —COOM or —SO$_3$M wherein M represents hydrogen or a salt-forming cation. Suitable salt-forming cations M are, in general, those of alkaline earth metals, for example of calcium, barium or magnesium, and particularly of alkali metals, for example of sodium or potassium, but also ammonium which is optionally substituted by alkyl or hydroxyalkyl having 1 to 4 carbon atoms, or amine salt ions of cyclic amines, such as pyridine, morpholine and piperidine. The potassium ion and the sodium ion are particularly preferred, besides hydrogen, in the meaning of M.

Particular mention is merited by the compounds of the formula

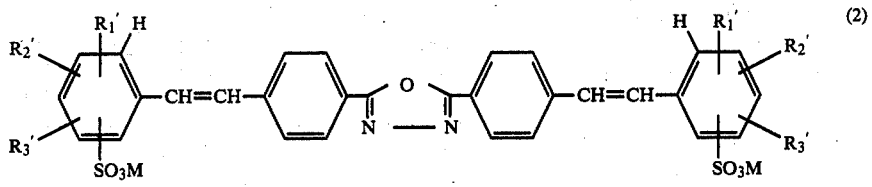

wherein $R'_1$ denotes hydrogen, alkyl having 1 to 4 carbon atoms, alkoxy having 1 to 4 carbon atoms, chlorine, sulpho, sulphophenyl, cyano, carboxyl or carbomethoxy, $R'_2$ denotes hydrogen, chlorine or alkyl having 1 to 4 carbon atoms, and $R'_3$ denotes hydrogen or methyl, as well as the compounds of the formula

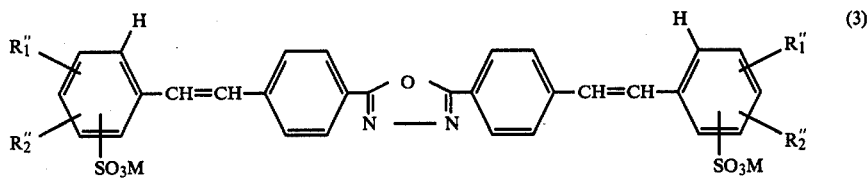

wherein $R''_1$ denotes hydrogen, methyl, ethyl, methoxy, chlorine, sulpho, cyano, carboxyl or carbomethoxy, and $R''_2$ denotes hydrogen, chlorine, methyl or ethyl.

Compounds of particular practical interest are those of the formula

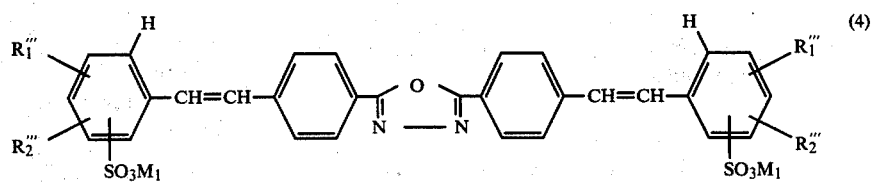

wherein $R'''_1$ denotes hydrogen, chlorine or sulpho, $R'''_2$ denotes hydrogen or chlorine, and $M_1$ denotes a hydrogen ion, sodium ion or potassium ion, and those of the formula

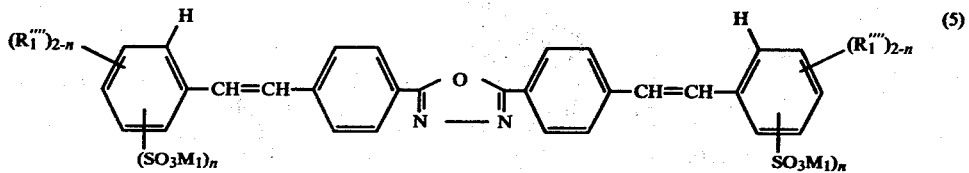

wherein $R''''_1$ denotes hydrogen, alkyl having 1 to 4 carbon atoms, alkoxy having 1 to 4 carbon atoms, or chlorine, $M_1$ denotes a hydrogen ion, sodium ion or potassium ion, and n denotes the number 1 or 2.

The present invention also relates to a process for the manufacture of the compounds of the formulae (1) to (5).

The process, according to the invention, for the manufacture of the compounds of the formula

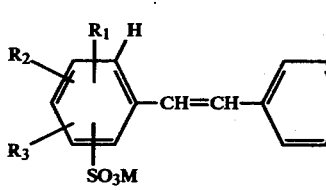

wherein $R_1$ denotes hydrogen, alkyl having 1 to 4 carbon atoms, alkoxy having 1 to 4 carbon atoms, chlorine, sulpho, sulphophenyl, cyano, carboxyl or carbalkoxy having 2 to 6 carbon atoms, $R_2$ denotes hydrogen, alkyl having 1 to 4 carbon atoms, alkoxy having 1 to 4 carbon atoms, or chlorine, $R_3$ denotes hydrogen or alkyl having 1 to 4 carbon atoms, and M denotes a hydrogen ion, alkali metal ion, alkaline earth metal ion, ammonium ion or amine salt ion, is characterised in that 1 mol of a compound of the formula

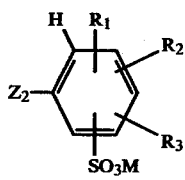

is reacted with 2 mols of a compound of the formula

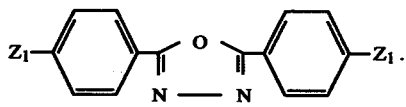

in which $R_1$, $R_2$, $R_3$ and M have the meaning indicated above and one of the symbols $Z_1$ and $Z_2$ denotes an O=CH group and the other denotes one of the groupings of the formulae

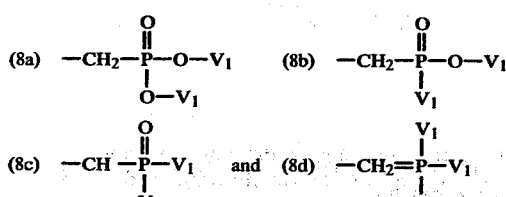

wherein $V_1$ represents an alkyl radical which is optionally further substituted, preferably such an alkyl radical having up to 6 carbon atoms, an aryl radical, preferably a phenyl radical, a cycloalkyl radical, preferably a cyclohexyl radical, or an aralkyl radical, preferably a benzyl radical.

Compounds of the formula (2) to (5) are obtained in a completely analogous manner by reacting a compound of the formula

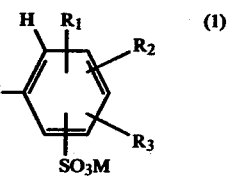

with a compound of the formula

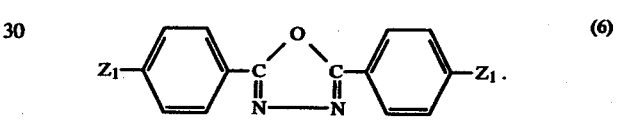

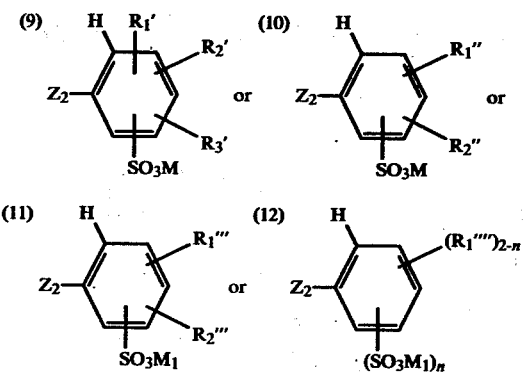

the substituents $R'_1$, $R'_2$, $R'_3$, $R''_1$, $R''_2$, $R'''_1$, $R'''_2$, $R''''_1$, M, $M_1$, $Z_1$ and $Z_2$ in the formulae (6) and (9) to (12) having the meanings indicated above.

In the preferred embodiment of the abovementioned manufacturing process, $Z_1$ represents a radical of the formulae (8a) to (8d), particularly (8a), and $Z_2$ accordingly represents the O=CH group.

The compounds of the formulae (6) to (12) which are required as starting materials can be manufactured in analogy to processes which are in themselves known.

The manufacturing process is advantageously carried out in inert solvents. Examples of these which may be mentioned are hydrocarbons, such as toluene and xylene, or alcohols, such as methanol, ethanol, isopropanol, butanol, glycols, glycol ethers, such as 2-methoxyethanol, hexanols, cyclohexanol and cyclooctanol, and also ethers, such as diisopropyl ether, tetrahydrofurane and dioxane, and dimethylsulphoxide, formamide and N-methylpyrrolidone. Polar organic solvent such as dimethylformamide and dimethylsulphoxide are particularly suitable. Some of the reactions can also be carried out in aqueous solution.

The temperature at which the reaction is carried out can vary within wide limits. It is determined:

(α) by the stability of the solvent used towards the reactants, particularly towards the strongly basic alkali metal compounds, (β) by the reactivity of the partners in the condensation and (γ) by the activity, as a condensation agent, of the combination solvent/base.

In practice, temperatures between about 10° and 100° C. are generally possible in this respect, particularly if dimethylformamide or dimethylsulphoxide is used as the solvent. The preferred temperature range is 20° to 60° C. However, under certain circumstances, higher temperatures can also be used, if this is desired for reasons of saving time, or a less active but cheaper condensation agent is to be employed; in principle, therefore, reaction temperatures in the range from 10° to 180° C. are also possible.

Possible strongly basic alkali metal compounds are above all the hydroxides, amides and alcoholates (preferably those of primary alcohols containing 1 to 4 carbon atoms) of the alkali metals, those of lithium, sodium and potassium being of predominant interest for economic reasons. In principle, however, and in particular cases, alkali metal sulphides and carbonates, aryl-alkali metal compounds, such as, for example, phenyl-lithium, or strongly basic amines (including ammonium bases, for example trialkylammonium hydroxides) can also be used successfully.

The new compounds defined above exhibit a more or less pronounced fluorescence in the dissolved or finely dispersed state. They can be used for optically brightening the most diverse synthetic, semi-synthetic or natural organic materials or substances which contain such organic materials.

The following groups of organic materials, where optical brightening thereof is relevant, may be mentioned as examples of the above, without the survey given below using intended to express any restriction thereto:

I. Synthetic organic high-molecular materials:

(a) Polymerisation products based on organic compounds containing at least one polymerisable carbon-carbon double bond, that is to say their homopolymers or copolymers as well as their after-treatment products such as, for example, crosslinking, grafting or degradation products, polymer blends or products obtained by modification of reactive groups, for example polymers based on α,β-unsaturated carboxylic acids or derivatives of such carboxylic acids, especially on acrylic compounds (such as, for example, acrylic esters, acrylic acid, acrylonitrile, acrylamides and their derivatives or their methacrylic analogues), on olefine hydrocarbons (such as, for example, ethylene, propylene, styrenes or dienes and also so-called ABS polymers), and polymers based on vinyl and vinylidene compounds (such as, for example, vinyl chloride, vinyl alcohol and vinylidene chloride), (b) Polymerisation products such as are obtainable by ring opening, for example, polyamides of the polycaprolactam type, and also polymers which are obtainable both via poly-addition and via polycondensation, such as polyethers or polyacetals, (c) Polycondensation products or precondensates based on bifunctional or polyfunctional compounds possessing condensable groups, their homocondensation and co-condensation products, and after-treatment products, such as, for example, polyesters, especially polyesters which are saturated (for example ethylene glycol terephthalic acid polyester) or unsaturated (for example maleic acid-dialcohol polycondensates as well as their crosslinking products with copolymerisable vinyl monomers), unbranched or branched (also including those based on polyhydric alcohols, such as, for example alkyd resins), polyamides (for example hexamethylenediamine adipate), maleate resins, melamine resins, their precondensates and analogues, polycarbonates and silicones, and (d) Polyaddition products such as polyurethanes (crosslinked and non-crosslinked) and epoxide resins. II. Semi-synthetic organic materials, for example, cellulose esters of varying degrees of esterification (so-called 2½-acetate or triacetate) or cellulose ethers, regenerated cellulose (viscose or cuprammonium cellulose), or their after-treatment products, and casein plastics. III. Natural organic materials of animal or vegetable origin, for example based on cellulose or proteins, such as cotton, wool, linen, silk, natural lacquer resins, starch and casein.

The organic materials to be optically brightened can be in the most diverse states of processing (raw materials, semi-finished goods or finished goods). On the other hand, they can be in the form of structures of the most diverse shapes, that is say, for example, predominantly three-dimensional bodies such as slabs, profiles, injection mouldings, various machined articles, chips, granules or foams, and also as predominantly two-dimensional bodies such as films, sheets, lacquers, coverings, impregnations and coatings, or as predominantly one-dimensional bodies such as filaments, fibres, flocks and wires. The said materials can, on the other hand, also be in an unshaped state, in the most diverse homogeneous or inhomogeneous forms of division, such as, for example, in the form of powders, solutions, emulsions, dispersions, latices, pastes or waxes.

Fibre materials can, for example, be in the form of continuous filaments (stretched or unstretched), staple fibres, flocks, hanks, textile filaments, yarns, threads, fibre fleeces, felts, waddings, flocked structures or woven textile fabrics, textile laminates, knitted fabrics and papers, cardboards or paper pulps.

The compounds to be used according to the invention are of importance, inter alia, for the treatment of organic textile materials, especially woven textile fabrics. Where fibres, which can be in the form of staple fibres or continuous filaments or in the form of hanks, woven fabrics, knitted fabrics, fleeces, flocked substrates or laminates, are to be optically brightened accordng to the invention, this is advantageously effected in an aqueous medium, wherein the compounds in question are present in a finely divided form (suspensions, so-called microdispersions or possibly solutions). If desired, dispersing agents, stabilisers, wetting agents and further auxiliaries can be added during the treatment.

Depending on the type of brightener compound used, it may prove advantageous to carry out the treatment in a neutral or alkaline or acid bath. The treatment is usually carried out at temperatures of about 20° to 140° C., for example at the boiling point of the bath or near it (about 90° C.). Solutions or emulsions in organic solvents can also be used for the finishing, according to the invention, of textile substrates, as is practised in the dyeing trade in so-called solvent dyeing (pad-thermofix application, or exhaustion dyeing process in dyeing machines).

The new optical brighteners according to the present invention can further be added to, or incorporated in, the materials before or during their shaping. Thus they can, for example, be added to the compression moulding composition or injection moulding composition during the manufacture of films, sheets (for example, hot milling into polyvinyl chloride) or mouldings.

Where fully synthetic or semi-synthetic organic materials are being shaped by spinning processes or via spinning compositions, the optical brighteners can be applied in accordance with the following processes:

Addition to the starting substances (for example monomers) or intermediates (for example precondensates or prepolymers), that is to say before or during the polymerisation, polycondensation or polyaddition, Powdering onto polymer chips or granules for spinning compositions, Bath dyeing of polymer chips or granules for spinning compositions, Metered addition to spinning melts or spinning solutions, and Application to the tow before stretching.

The new optical brighteners according to the present invention can, for example, also be employed in the following use forms:

(a) Mixed with dyestuffs (shading) or pigments (coloured pigments or especially, for example, white pigments), or as an additive to dye baths, printing pastes, discharge pastes or reserve pastes, or for the after-treatment of dyeings, prints or discharge prints.

(b) Mixed with so-called "carriers", wetting agents, plasticisers, swelling agents, anti-oxidants, light stabilisers, heat stabilisers and chemical bleaching agents (chlorite bleach or bleaching bath additives).

(c) Mixed with crosslinking agents or finishing agents (for example starch or synthetic finishes), and in combination with the most diverse textile finishing processes, especially synthetic resin finishes (for example creaseproof finishes such as "wash-and-wear", "permanent-press" or "no-iron"), as well as flameproof finishes, soft handle finishes, anti-soiling finishes or anti-static finishes, or anti-microbial finishes.

(d) Incorporation of the optical brighteners into polymeric carriers (polymerisation, polycondensation or polyaddition products), in a dissolved or dispersed form, for use, for example in coating agents, impregnating agents or binders (solutions, dispersions and emulsions) for textiles, fleeces, paper and leather.

(e) As additives to so-called "master batches".

(f) As additives to the most diverse industrial products in order to render these more marketable (for example improving the appearance of soaps, detergents and pigments), (g) In combination with other optically brightening substances, (h) In spinning bath preparations, that is to say as additives to spinning baths such as are used for improving the slip for the further processing of synthetic fibres, or from a special bath before stretching the fibre.

(i) As scintillators for various purposes of a photographic nature, such as, for example, for electrophotographic reproduction or supersensitisation, and for the optical brightening of photographic layers, optionally in combination with white pigments such as, for example, $TiO_2$.

If the brightening process is combined with textile treatment methods or finishing methods, the combined treatment can in many cases advantageously be carried out with the aid of appropriate stable preparations which contain the optically brightening compounds in such concentration that the desired brightening effect is achieved.

In certain cases, the brighteners are made fully effective by an after-treatment. This can, for example, represent a chemical treatment (for example acid treatment), a thermal treatment (for example heat) or a combined chemical/thermal treatment. Thus, for example, the appropriate procedure to follow in optically brightening a range of fibre substrates, for example polyester fibres, with the brighteners according to the invention, is to impregnate these fibres with the aqueous dispersions (or optionally also solutions) of the brighteners at temperatures below 75° C., for example at room temperature, and to subject them to a dry heat treatment at temperatures above 100° C., it being generally advisable additionally to dry the fibre material beforehand at a moderately elevated temperature, for example at not less than 60° C. and up to about 130° C. The heat treatment in the dry state is then advantageously carried out at temperatures between 120° and 225° C., for example by heating in a drying chamber, by ironing within the specified temperature range or by treatment with dry, superheated steam. The drying and dry heat treatment can also be carried out in immediate succession or be combined in a single process stage.

The amount of the new optical brighteners to be used according to the invention, relative to the material to be optically brightened, can vary within wide limits. A distinct and durable effect is already achievable with very small amounts, in certain cases, for example, amounts of 0.0001 percent by weight. However, amounts of up to about 0.8 percent by weight and optionally of up to about 2 percent by weight can be employed. For most practical purposes, amounts between 0.0005 and 0.5 percent by weight are of preferred interest.

The new optical brighteners are also particularly suitable for use as additives for wash liquors or industrial and domestic washing agents, to which they can be added in various ways. They are appropriately added to wash liquors in the form of their solutions in water or organic solvents or in a finely divided form, as aqueous dispersions. They are advantageously added to domestic or industrial washing agents in any stage of the manufacturing process of the washing agents, for example to the so-called "slurry" before spray-drying to the washing powder, or during the preparation of liquid washing agent combinations. They can be added either in the form of a solution or dispersion in water or other solvents or, without auxiliaries, as a dry brightening powder. For example, the brighteners can be mixed, kneaded or ground with the detergent substances and, in this form, admixed to the finished washing powder. However, they can also be sprayed in a dissolved or predispersed form onto the finished washing agent.

Possible washing agents are the known mixtures of detergent substances such as, for example, soap in the form of chips and powders, synthetics, soluble salts of sulphuric acid half esters of higher fatty alcohols, arylsulphonic acids with higher and/or multiple alkyl substituents, sulphocarboxylic acid esters of medium to higher alcohols, fatty acid acylaminoalkyl- or acylaminoaryl-glycerolsulphonates, phosphoric acid esters of fatty alcohols and the like. Possible so-called "builders" which can be used are, for example, alkali metal polyphosphates and polymetaphosphates, alkali metal pyrophosphates, alkali metal salts of carboxymethylcellulose and other "soil redeposition inhibitors", and also alkali metal silicates, alkali metal carbonates, alkali metal borates, alkali metal perborates, nitrilotriacetic acid, ethylenediaminotetraacetic acid, and foam stabilisers, such as alkanolamides of higher fatty acids. The washing agents can further contain, for example: antistatic agents, skin protection agents which restore fat, such as lanolin, enzymes, anti-microbial agents, perfumes and dyestuffs.

The new optical brighteners have the particular advantage that they are also active in the presence of active chlorine donors, such as, for example, hypochlorite, and can be used without significant loss of the effects in wash liquors containing non-ionic washing agents, for example alkylphenol polyglycol ethers.

The compounds according to the invention are added in amounts of 0.005–1% or more, relative to the weight of the liquid or pulverulent, finished washing agent. Wash liquors which contain the indicated amounts of the optical brighteners claimed impart a brilliant appearance in daylight when used to wash textiles of cellulose fibres, polyamide fibres, cellulose fibres with a high quality finish, polyester fibres, wool and the like.

The washing treatment is carried out, for example, as follows:

The textiles quoted are treated for 1 to 30 minutes at 20° to 100° C. in a washing liquor which contains 1 to 10 g/kg of a composite washing agent containing a builder and 0.05 to 1%, relative to the weight of washing agent, of the brighteners claimed. The liquor ratio can be 1:3 to 1:50. After washing, rinsing and drying are carried out as usual. The washing liquor can contain 0.2 g/l of active chlorine (for example as hypochlorite) or 0.1 to 2 g/l of sodium perborate, as a bleaching additive.

In the examples, unless otherwise specified, percentages are always percentages by weight. Unless otherwise noted, melting points and boiling points are uncorrected.

EXAMPLE 1

20 g of a 15% strength solution of sodium methylate in methanol are added dropwise over the course of about 5 minutes to a solution of 13.0 g of the compound of the formula

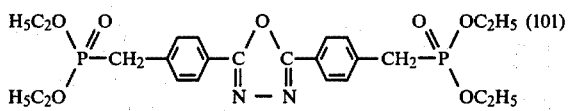

and 12.2 g of 4-methylbenzaldehyde-3-sulphonic acid (sodium salt) in 150 ml of dimethylsulphoxide, while stirring well and passing nitrogen over the mixture, the temperature rising from 20° C. to 37° C. The reaction mixture is then stirred for a further hour at 40° to 45° C., poured into 1.3 liters of water at 70° C., and clarified by filtration and the clear solution is treated, at 70° C., with one liter of alcohol and 65 g of sodium chloride are added slowly. The product which crystallises out is filtered off after cooling and recrystallised from a mixture of 400 ml of water and 400 ml of alcohol.

This gives 7.2 g of the compound of the formula

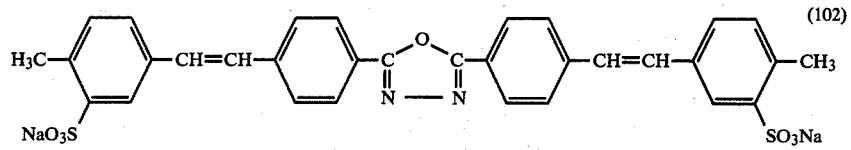

as a light yellow crystalline powder.

The compound of the formula (101) can be obtained as follows:

105.5 g of N-bromosuccinimide and 2.5 g of dibenzoyl peroxide are introduced in portions over the course of about 30 minutes and at about 75° C. into a solution of 74 g of the oxdiazole of the formula

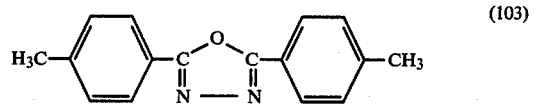

and 0.5 g of dibenzoyl peroxide in 2,000 ml of carbon tetrachloride, while stirring well and irradiating with a UV lamp. The mixture is then boiled under reflux for about a further 5 hours. After cooling, the product which has crystallised out is filtered off with suction and is washed with a little alcohol and then with about 10 liters of hot water. After drying the residue at 80° to 85° C. in vacuo, 81.3 g of the compound of the formula

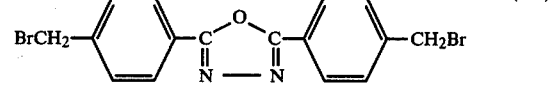

are obtained. Melting point: 218° to 219° C.

81.0 g of the compound (104) are introduced in portions, while stirring well, over the course of about 30 minutes and at about 135° C. into 400 ml of triethyl phosphite. The mixture is then stirred for about a further 4 hours at 145° C., ethyl bromide distilling off. After cooling, the product which has crystallised out is filtered off with suction, washed with a little n-hexane and dried in vacuo at 50° to 55° C. This gives 85.9 g of the compound (101) of melting point 107° to 109° C.

EXAMPLE 2

A homogeneous mixture of 26.1 g of the compound of the formula (101) and 33.4 g of the disodium salt of benzaldehyde-2,4-disulphonic acid (92.7% strength) is introduced in portions, at 40° to 45° C. and over the course of about 15 minutes, into a suspension of 6.2 g of sodium methylate (96.0% strength) in 200 ml of dimethylformamide, while stirring well and passing nitrogen over the mixture. The mixture is then stirred for about a further 3 hours at 40° to 45° C. The reaction mixture is evaporated in vacuo to dryness, the residue is dissolved in 350 ml of boiling water, treated with 1,050 ml of alcohol, clarified by hot filtration and cooled, and the product which has crystallised out is filtered off with suction and dried in vacuo at 100° to 110° C.

This gives 16.7 g of the compound of the formula

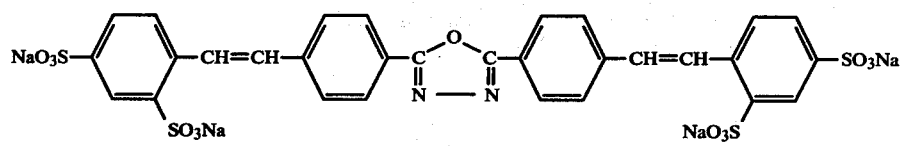

(105)

as a light yellow crystalline powder.

The compounds listed in the table which follows can be prepared in the form of their potassium salts, sodium salts or the salts indicated, in a manner similar to that described above.

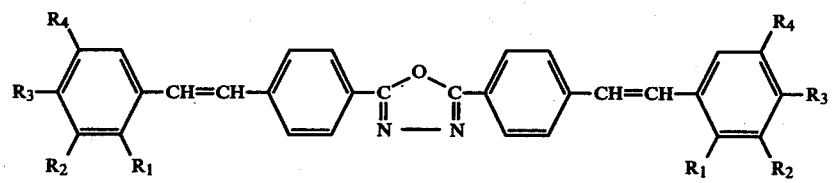

Table

| Formula No. | $R_1$ | $R_2$ | $R_3$ | $R_4$ |
|---|---|---|---|---|
| 106 | $SO_3H$ | H | H | H |
| 107 | H | $SO_3H$ | H | H |
| 108 | H | H | $SO_3H$ | H |
| 109 | $SO_3H$ | H | H | $SO_3H$ |
| 110 | Cl | H | H | $SO_3H$ |
| 111 | H | $SO_3H$ | Cl | H |
| 112 | $SO_3H$ | H | Cl | H |
| 113 | $SO_3H$ | H | H | Cl |
| 114 | Cl | H | Cl | $SO_3H$ |
| 115 | H | Cl | Cl | $SO_3H$ |
| 116 | $CH_3$ | H | H | $SO_3H$ |
| 117 | H | $CH_3$ | H | $SO_3H$ |
| 118 | $CH_3$ | H | $CH_3$ | $SO_3H$ |
| 119 | $CH_3$ | $SO_3H$ | H | $CH_3$ |
| 120 | $CH_3$ | $SO_3H$ | $CH_3$ | $CH_3$ |
| 121 | $CH_3$ | $CH_3$ | $CH_3$ | $SO_3H$ |
| 122 | $CH_2-CH_3$ | H | $CH_2-CH_3$ | $SO_3H$ |
| 123 | H | Cl | $CH_3$ | $SO_3H$ |
| 124 | H | $SO_3H$ | $CH_3O$ | H |
| 125 | $CH_3O$ | H | H | $SO_3H$ |
| 126 | $CH_3O$ | $CH_3O$ | H | $SO_3H$ |
| 127 | $SO_3H$ | H | CN | H |
| 128 | $SO_3H$ | H | COOH | H |
| 129 | $SO_3H$ | H | $COOCH_3$ | H |
| 130 | H | H | –⟨⟩–$SO_3H$ | H |
| 131 | H | H | –⟨⟩–$SO_3H.N⟨⟩$ | H |

EXAMPLE 3

A bleached cotton material is washed for 15 minutes, with a liquor ratio of 1:20, in a liquor warmed to 50° C. and containing the following additives per liter:

0.004 g of one of the brighteners of the formulae (102) or (106),
0.25 g of active chlorine (Javelle water) and
4 g of a washing powder of the following composition:
15.00% of dodecylbenzenesulphonate,
10.00% of sodium laurylsulphonate,
40.00% of sodium tripolyphosphate,
25.75% of anhydrous sodium sulphate,
7.00% of sodium metasilicate,
2.00% of carboxymethylcellulose and
0.25% of ethylenediamine-tetraacetic acid.

The cotton material is not introduced into the bath until 15 minutes after the preparation of the washing liquor warmed to 50° C. After rinsing and drying, the fabric exhibits a good brightening effect with good fastness to chlorine.

The washing powder of the composition indicated above can also contain the brightener of the formulae indicated above in a directly incorporated form.

EXAMPLE 4

A polyamide fibre fabric (Perlon) is introduced, at a liquor ratio of 1:40 and at 60° C., into a bath which contains (relative to the weight of material) 0.05% of a brightener of the formula (102), (105) or (106) as well as, per liter, 1 g of 80% strength acetic acid and 0.25 g of an addition reaction product of 30 to 35 mols of ethylene oxide with one mol of technical stearyl alcohol. The mixture is warmed to the boil over the course of 30 minutes and is kept at the boil for 30 minutes. After rinsing and drying, a good brightening effect is obtained.

Similar brightening effects are obtained if, instead of the fabric of polyamide 6, a fabric of polyamide 66 (nylon) is used.

Finally, it is also possible to work under high temperature conditions, for example for 30 minutes at 130° C. An addition of 3 g/l of hydrosulphite is advisable for this mode of application.

EXAMPLE 5

10,000 g of a polyamide prepared in a known manner from hexamethylenediamine adipate are mixed, in the form of chips, in a tumbler with 30 g of titanium dioxide (rutile modification) and 5 g of the compound of the formula (102), (105) or (106) for 12 hours. The chips treated in this way are melted, after displacing the atmospheric oxygen by steam, in a kettle heated to 300° to 310° C. by means of oil or diphenyl vapour, and are stirred for half an hour. The melt is then pressed out through a spinneret under a nitrogen pressure of 5 atmospheres gauge, and the filament spun in this manner is cooled and wound up on a spinning bobbin. The resulting filaments exhibit a good brightening effect.

Similarly good results are obtained if, instead of a polyamide prepared from hexamethylenediamine adipate, a polyamide prepared from ε-caprolactam is used.

EXAMPLE 6

A bleached cotton material is washed for 30 minutes at 95° C. at a liquor ratio of 1:20. The washing liquor contains the following additives per liter:
0.004 g of the brightener of the formula (102) or (106) and
4 g of a washing powder of the following composition:
40.0% of soap flakes,
15.0% of sodium tripolyphosphate,
8.0% of sodium perborate,
1.0% of magnesium silicate,
11.0% of sodium metasilicate (9 H$_2$O),
24.6% of calcined sodium carbonate and
0.4% of ethylenediamine-tetraacetic acid.
After rinsing and drying, the cotton fabric has a good brightening effect.

What we claim is:
1. A distilbenyl-oxdiazole of the formula

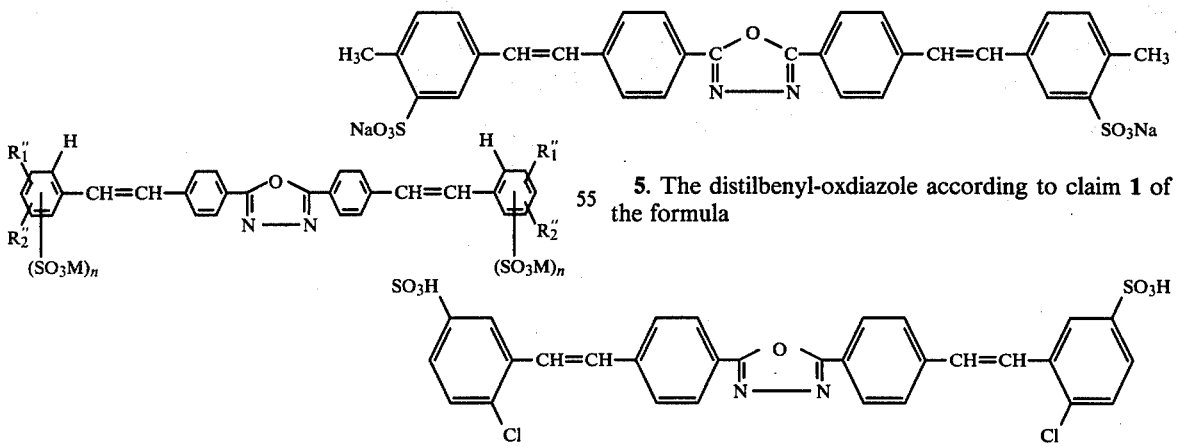

wherein each of
R$'_1$' is identical and denotes methyl, ethyl, methoxy, chlorine, cyano, caboxyl or carbomethoxy and each of
R$'_2$' is identical and denotes hydrogen, chlorine, methyl or ethyl,
M denotes a hydrogen ion, alkali metal ion, alkaline earth metal ion, ammonium ion or amine salt ion and n denotes the numbers 1 or 2.

2. A distilbenyl-oxdiazole according to claim 1 of the formula

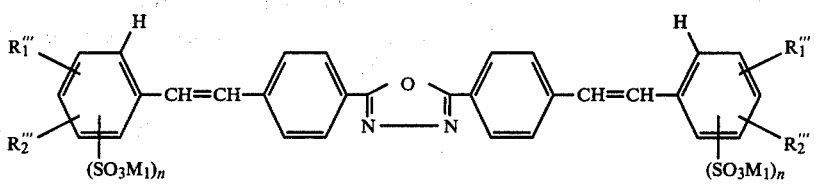

wherein each of
R$'_1$'' is identical and denotes hydrogen or chlorine, each of R$'_2$'' is identical and denotes hydrogen or chlorine, and
wherein at least one of of R$'_1$'' or R$'_2$'' is chlorine and M$_1$ denotes a hydrogen ion, sodium ion or potassium ion and n denotes 1 or 2.

3. A distilbenyl-oxdiazole according to claim 1, of the formula

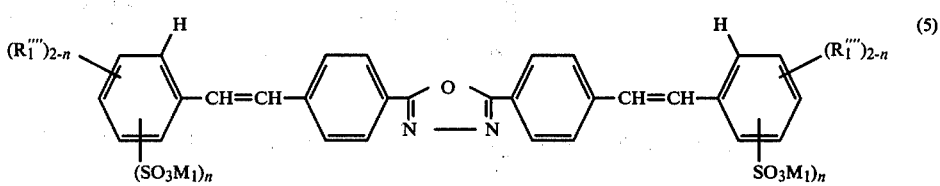

wherein R''''$_1$ denotes alkyl having 1 to 4 carbon atoms, alkoxy having 1 to 4 carbon atoms, or chlorine, M$_1$ denotes a hydrogen ion, sodium ion or potassium ion, and n denotes the number 1 or 2.

4. The distilbenyl-oxdiazole according to claim 1 of the formula

5. The distilbenyl-oxdiazole according to claim 1 of the formula

6. The distilbenyl-oxdiazole according to claim 1 of the formula

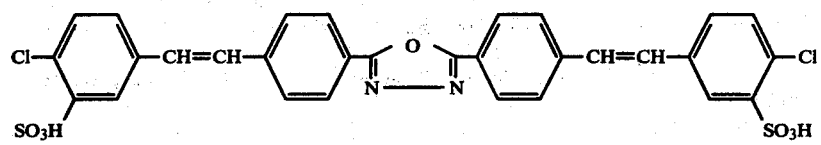
7. The distilbenyl-oxdiazole according to claim 1 of the formula
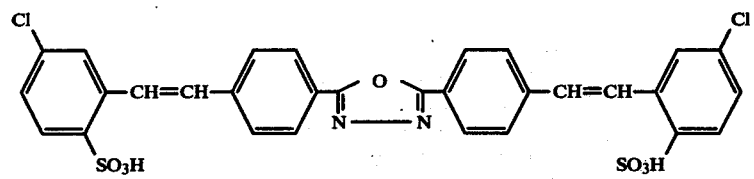
8. The distilbenyl-oxdiazole according to claim 1 of the formula
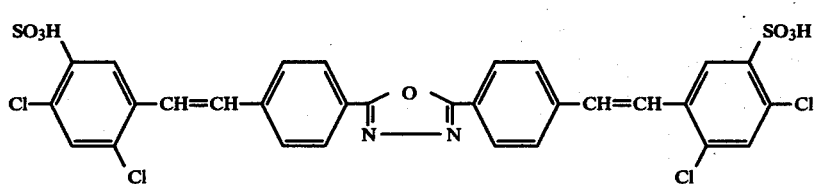
9. The distilbenyl-oxdiazole of the formula
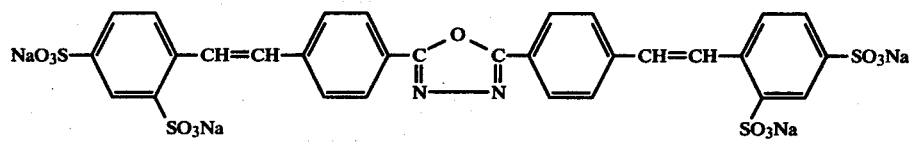
10. The distilbenyl-oxdiazole of the formula
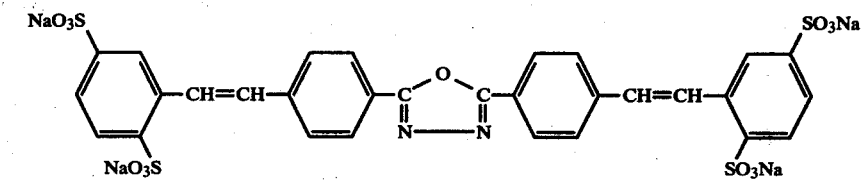
11. The distilbenyl-oxdiazole of the formula
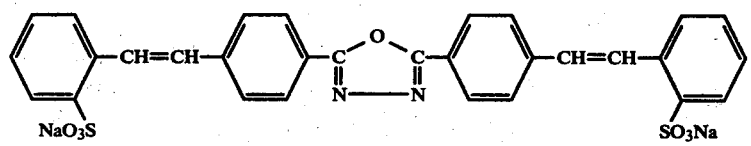
* * * * *